United States Patent
Korfhage et al.

(10) Patent No.: US 9,074,248 B1
(45) Date of Patent: Jul. 7, 2015

(54) PRIMERS FOR HELICASE DEPENDENT AMPLIFICATION AND THEIR METHODS OF USE

(71) Applicant: QIAGEN GmbH, Hilden (DE)

(72) Inventors: Christian Korfhage, Langenfeld (DE); Sven van Ooyen, Bad Neuenahr (DE)

(73) Assignee: QIAGEN GMBH, Hilden (DE)

( * ) Notice: Subject to any disclaimer, the term of this patent is extended or adjusted under 35 U.S.C. 154(b) by 183 days.

(21) Appl. No.: 13/718,102

(22) Filed: Dec. 18, 2012

(51) Int. Cl.
  *C12P 19/34* (2006.01)
  *C12Q 1/68* (2006.01)
(52) U.S. Cl.
  CPC .................................. *C12Q 1/6853* (2013.01)
(58) Field of Classification Search
  CPC ....................................................... C12Q 1/6853
  USPC ................................................. 435/91.2, 6.1
  See application file for complete search history.

(56) References Cited

U.S. PATENT DOCUMENTS

| | | | |
|---|---|---|---|
| 6,214,587 B1 | 4/2001 | Dattagupta et al. | |
| 6,973,388 B2 | 12/2005 | Friend et al. | |
| 7,282,328 B2 | 10/2007 | Kong et al. | |
| 2010/0304442 A1* | 12/2010 | Kutyavin | 435/91.2 |
| 2014/0017730 A1* | 1/2014 | Hicke et al. | 435/91.2 |

FOREIGN PATENT DOCUMENTS

| WO | WO 01/25473 | 4/2001 |
|---|---|---|
| WO | WO 02/02740 | 1/2002 |

OTHER PUBLICATIONS

Collins and McCarthy, "Purification and characterization of *Thermus themophiles* UvrD," *Extremophiles*, 7:35-41 (2003).
Dong et al., "A coupled complex of T4 DNA replication helicase (gp41) and polymerase (gp43) can perform rapid and processive DNA strand-displacement synthesis," *Proc. Natl. Acad. Sci. USA* 93:14456-14461 (1996).
Grainge et al., "Biochemical analysis of components of the pre-replication complex of *Archaeoglobus fulgidus*," *Nucleic Acids Res.* 31:4888-4898 (2003).
Harmon and Kowalczykowski, "Biochemical Characterization of the DNA Helicase Activity of the *Escherichia coli* RecQ Helicase," *J. Biol. Chem.* 276:232-243 (2001).
Jessing et al., "Evaluation of a Multiplex PCR Test for Simultaneous Identification and Serotyping of *Actinobacillus pleuropneumoniae* Serotypes 2, 5, and 6," *J. Clin. Microbiol.* 41:4095-4100 (2003).
Käempke et al., "Efficient primer design algorithyms," *Bioinformatics* 17:214-225 (2001).
Kaplan and Steitz, "DuaB from *Thermus aquaticus* Unwinds Forked Duplex DNA with an Asymmetric Tail Length Dependence," *J. Biol. Chem.* 274:6889-6897 (1999).
Mechanic et al., "*Escherichia coli* MutL Loads DNA Helicase II onto DNA," *J. Biol. Chem.* 275:38337-38346 (2000).
Miyoshi et al., "Molecular Crowding Regulates the Structural Switch of the DNA G-Quadruplex," *Biochemistry* 41:15017-15024 (2002).
Yamaguchi et al., "MutS and MutL Activate DNA Helicase II in a Mismatch-dependent Manner," *J. Biol. Chem.* 273:9197-9201 (1998).

* cited by examiner

*Primary Examiner* — Cynthia B Wilder
(74) *Attorney, Agent, or Firm* — Fanelli Haag PLLC

(57) ABSTRACT

It has been unexpectedly and surprisingly found that Helicase Dependent Amplification (HDA) primers having termini enriched for A or C at the 5'-ends, result in a much more efficient HDA reaction than those primers having G or T rich 5'-ends. Since A is a low melting base and C is a high-melting base, the melting characteristic of primer termini is not correlated with melting characteristics of amplicon termini. Optimized HDA primers, methods of making and using optimized primers, as well as methods of as well as kits for optimized HDA are disclosed.

8 Claims, 3 Drawing Sheets

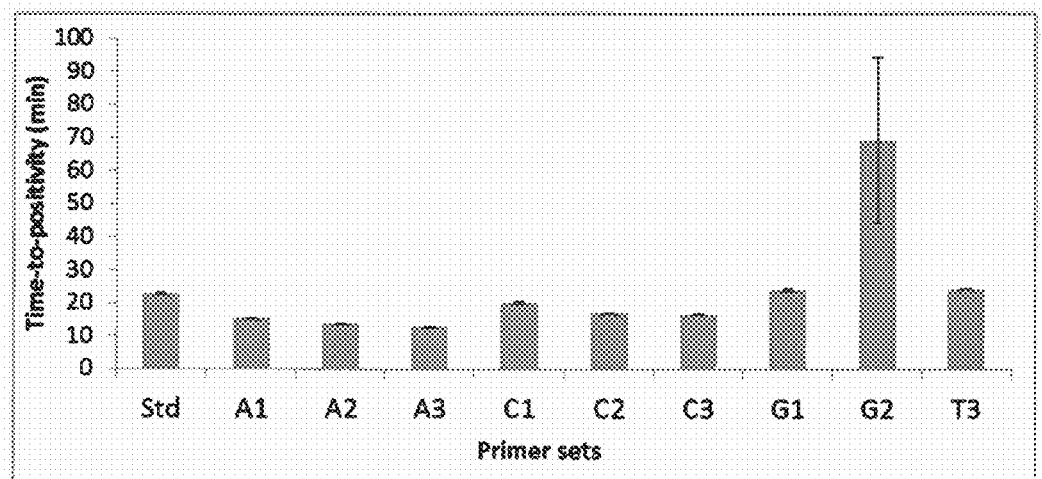

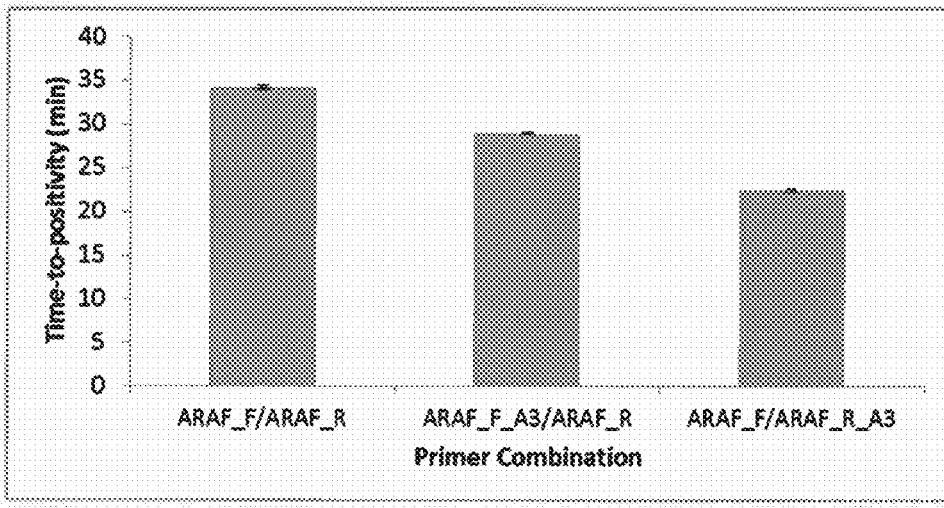

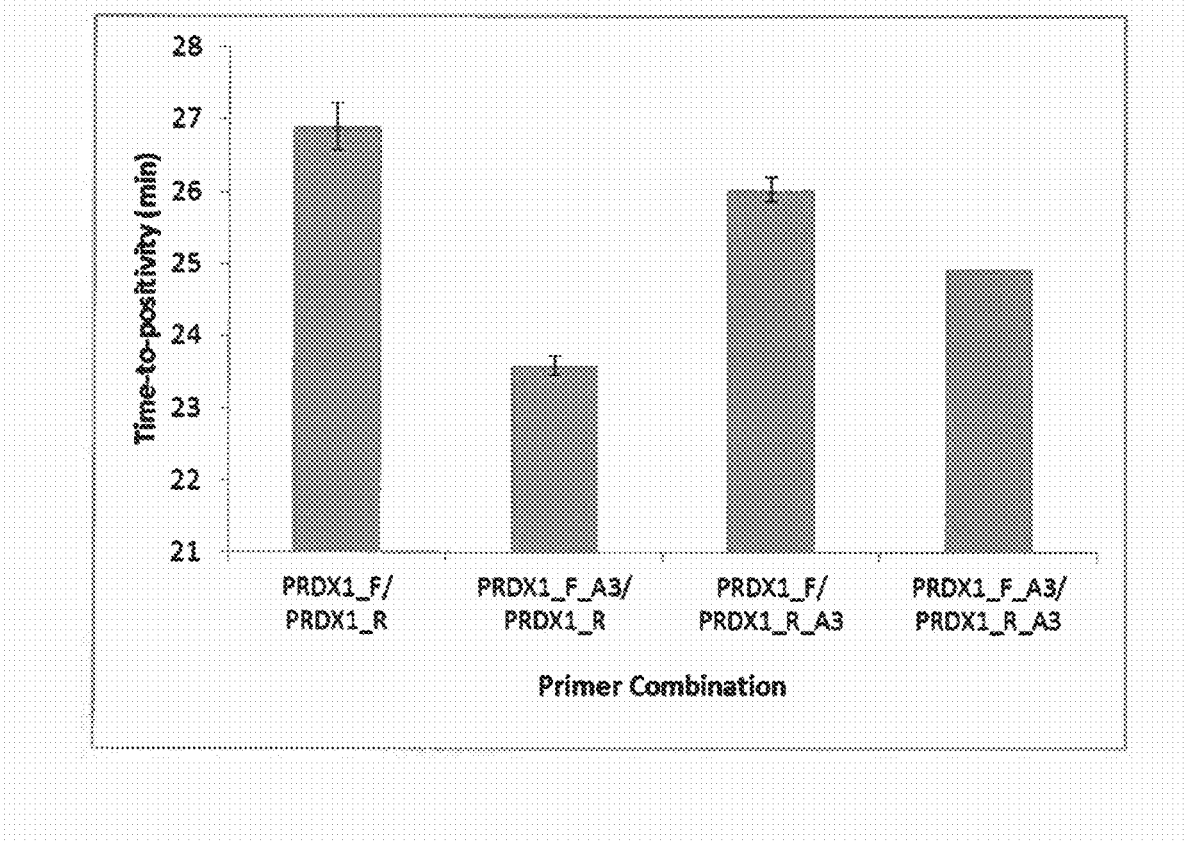

SEQUENCE LISTING

```
<160> NUMBER OF SEQ ID NOS: 46

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcgtttggca ccgtgtttc                                                19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggacacctt gagcaccttc                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcgtttggc accgtgtttc                                               20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agggacacct tgagcacctt c                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
aatcgtttgg caccgtgttt c                                              21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagggacacc ttgagcacct tc                                             22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaatcgtttg gcaccgtgtt tc                                             22

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaagggacac cttgagcacc ttc                                            23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctcgtttggc accgtgtttc                                                20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgggacacct tgagcacctt c                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
cctcgtttgg caccgtgttt c                                              21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccgggacacc ttgagcacct tc                                             22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccctcgtttg gcaccgtgtt tc                                             22

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccgggacac cttgagcacc ttc                                            23

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtcgtttggc accgtgtttc                                                20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggggacacct tgagcacctt c                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
```

```
ggtcgtttgg caccgtgttt c                                              21
```

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
gggggacacc ttgagcacct tc                                             22
```

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
ttttcgtttg gcaccgtgtt tc                                             22
```

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
tttgggacac cttgagcacc ttc                                            23
```

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21

```
cggtggcatg gcgatgtggc cgt                                            23
```

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
tcgtttggca ccgtgtttc                                                 19
```

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gggacacctt gagcaccttc                                          20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaatcgtttg gcaccgtgtt tc                                       22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aaagggacac cttgagcacc ttc                                      23

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgggacccat gaacattcct t                                        21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccctgaacga gatgccttca t                                        21

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaatgggacc catgaacatt cctt                                     24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aaaccctgaa cgagatgcct tcat                                     24

```
<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcgtttggca ccgtgtttc                                              19

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31 gggacaccتt gagcaccttc                                             20
```

<200> SEQ ID NO 31 sequence line (corrected):

```
gggacacctt gagcaccttc                                             20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
atcgtttggc accgtgtttc                                             20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agggacacct tgagcacctt c                                           21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aatcgtttgg caccgtgttt c                                           21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aagggacacc ttgagcacct tc                                          22
```

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
aaatcgtttg gcaccgtgtt tc                                           22

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
aaagggacac cttgagcacc ttc                                          23

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
aaaatcgttt ggcaccgtgt ttc                                          23

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
aaaagggaca ccttgagcac cttc                                         24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
aaaaatcgtt tggcaccgtg tttc                                         24

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic probe

<400> SEQUENCE: 41
agacccgaag cgcaccattg ctcaggat                                     28

```
<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaaaagggac accttgagca ccttc                                              25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aaaaaatcgt ttggcaccgt gtttc                                              25

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaaaaaggga caccttgagc accttc                                             26

<210> SEQ ID NO 45
<211> LENGTH: 4
<212> TYPE: PRT
<213> ORGANISM: Homo sapiens

<400> SEQUENCE: 45

Asp Glu Ala His
1

<210> SEQ ID NO 46
<211> LENGTH: 4
<212> TYPE: PRT
<213> ORGANISM: Homo sapiens

<400> SEQUENCE: 46

Asp Glu Ala Asp
1
```

PRIMERS FOR HELICASE DEPENDENT AMPLIFICATION AND THEIR METHODS OF USE

SEQUENCE LISTING

The instant application contains a Sequence Listing which has been submitted in ASCII format via EFS-Web and is hereby incorporated by reference in its entirety. Said ASCII copy, created on May 10, 2013, is named 0051-0140-US1_SL.txt and is 10,425 bytes in size.

FIELD OF THE INVENTION

This invention is related to the area of nucleic acid amplification in general and helicase-dependent amplification methods, compositions and kits.

BACKGROUND OF THE INVENTION

The polymerase chain reaction (PCR) is the most widely used method for in vitro DNA amplification for purposes of molecular biology and biomedical research. This process involves the separation of the double-stranded DNA in high heat into single strands (the denaturation step, typically achieved at 95-97° C.), annealing of the primers to the single stranded DNA (the annealing step) and copying the single strands to create new double-stranded DNA. PCR is commonly carried out in bench-top machines that are large, expensive, costly to run and maintain. This can limit the potential applications of DNA amplification in situations outside the laboratory (e.g., in the identification of potentially hazardous micro-organisms at the scene of investigation or at the point of care of a patient). In vivo, DNA is replicated by DNA polymerases with various accessory proteins, including a DNA helicase that acts to separate the DNA by unwinding the DNA double helix. Helicase-dependent-amplification (HDA) was developed using a helicase (an enzyme) to denature the DNA.

In HDA, strands of double stranded DNA are first separated by a DNA helicase and coated upon by single stranded DNA (ssDNA)-binding proteins. In the second step, two sequence specific primers hybridize to each border of the DNA template. DNA polymerases are then used to extend the primers annealed to the templates to produce a double stranded DNA. The two newly synthesized DNA products are then used as substrates by DNA helicases, entering the next round of the reaction. Thus, a simultaneous chain reaction develops, resulting in exponential amplification of the selected target sequence.

As opposed to PCR, the HDA process takes place at a constant (isothermic) incubation temperature and does not require a bench-top thermocycler. However, as the enzyme helicase facilitates strand separation, it is limiting during reaction kinetics. The helicase used for HDA is of the UvrD type of *E. coli*. Homologue thermostabile helicases may also be used (tHDA).

During HDA, the substrate of the helicase is the double stranded amplicon which is generated during the amplification reaction. Because the helicase cannot facilitate strand separation from the middle of a dsDNA fragment, the structure of the ends of the amplicon are very important. The ends of an amplicon are defined by the primers designed for a given template. Consequently, primer design is crucial for helicase kinetics and overall HDA reaction success.

U.S. application Ser. No. 10/665,633 describes factors to be considered in HDA primer design. Generally, primer pairs suitable for use in HDA are short synthetic oligonucleotides, for example, having a length of more than 10 nucleotides and less than 50 nucleotides. Oligonucleotide primer design involves various parameters such as string-based alignment scores, melting temperature, primer length and GC content (Kampke et al., Bioinformatics 17:214 225 (2003)). When designing a primer, one of the important factors is to choose a sequence within the target fragment which is specific to the nucleic acid molecule to be amplified. The other important factor is to decide the melting temperature of a primer for HDA reaction. The melting temperature of a primer is determined by the length and GC content of that oligonucleotide. Preferably the melting temperature of a primer is about 10 to 30° C. higher than the temperature at which the hybridization and amplification will take place. For example, if the temperature of the hybridization and amplification is set at 37° C. when using the *E. coli* UvrD helicase preparation, the melting temperature of a pair of primers designed for this reaction should be in a range between about 47° C. to 67° C. If the temperature of the hybridization and amplification is 60° C., the melting temperature of a pair of primers designed for that reaction should be in a range between 65° C. and 90° C. To choose the best primer for a HDA reaction, a set of primers with various melting temperatures can be tested in parallel assays. More information regarding primer design is described by Kampke et al., Bioinformatics 17:214 225 (2003).

Hairpin structures within primers may reduce primer binding kinetics which in turn, can affect efficiency and speed of the amplification process. Self-complementarity of primers can result in nonspecific primer-dimer amplicons that compete with the amplification of the specific target amplification. As such, primer specificity, melting characteristics, hairpin structures, self-complementarity must all be taken into account when designing HDA primers.

There is a need in the art for better HDA primers and methods of their use and design.

SUMMARY OF THE INVENTION

One aspect of the invention relates to methods of designing a primer to be used in helicase dependent amplification (HDA) of a template nucleic acid comprising generating or obtaining a nucleic acid sequence suitable for use as a primer in HDA to obtain an HDA primer sequence; and modifying the HDA primer sequence by adding, subtracting or substituting nucleotide bases in the HDA primer's 5' terminal sequence to obtain a modified HDA primer, wherein the modified HDA primer has between three and six M bases at its 5' terminus; wherein M is adenosine or cytosine.

In one embodiment of this aspect of the invention, the HDA is multiplex HDA. In another embodiment, the HDA is singleplex HDA. In another embodiment, the modified HDA primer is a forward primer. In yet another embodiment, the modified HDA primer is a reverse primer. In yet another embodiment, both the forward and reverse primers are modified HDA primers.

In multiplex HDA there are about or at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more sets of forward and reverse primers whereas in singleplex HDA there is only one set of forward and reverse primers.

In yet a further embodiment, the modified HDA primer is completely complementary to the template. In a further embodiment, the modified HDA primer is partially complementary to the template. In still a further embodiment, the modified HDA primer sequence is the same as the HDA primer sequence. In another embodiment, the modified HDA primer has greater amplification efficiency than the HDA primer. In still another embodiment, the modified HDA primer has between three and six adenosine bases at its 5' terminus. In still another embodiment, the modified HDA primer has between four and six adenosine bases at its 5' terminus. In yet a further embodiment, the modified HDA primer has either five or six adenosine bases at its 5' terminus. In yet another embodiment, the modified HDA primer has either three or four adenosine bases at its 5' terminus. In still another embodiment, the modified HDA primer has either four or five adenosine bases at its 5' terminus. In still another embodiment, the modified HDA primer has between four and six adenosine bases at its 5' terminus. In still a further embodiment, the modified HDA primer has between three and six cytosine bases at its 5' terminus. In yet a further embodiment, the modified HDA primer has between four and six cytosine bases at its 5' terminus. In yet a further embodiment, the modified HDA primer has either five or six cytosine bases at its 5' terminus. In yet a further embodiment, the modified HDA primer has either three or four cytosine bases at its 5' terminus. In yet a further embodiment, the modified HDA primer has either four or five cytosine bases at its 5' terminus. In yet a further embodiment, the modified HDA primer has between four and six M bases at its 5' terminus. In yet a further embodiment the modified HDA primer has either five or six M bases at its 5' terminus. In yet a further embodiment modified HDA primer has either three or four M bases at its 5' terminus. In yet a further embodiment the modified HDA primer has either four or five M bases at its 5' terminus In still another embodiment the modified HDA primer is 10% more efficient than the HDA primer sequence in a time-to-positivity assay. In still another embodiment the modified HDA primer is at least or about 10% more efficient than the HDA primer sequence in a time-to-positivity assay. In still another embodiment the modified HDA primer is at least or about 20% more efficient than the HDA primer sequence time-to-positivity assay. In still another embodiment n the modified HDA primer is at least or about 30% more efficient than the HDA primer sequence in a time-to-positivity assay. In still another embodiment the modified HDA primer is at least or about 40% more efficient than the HDA primer sequence in a time-to-positivity assay. In still another embodiment the modified HDA primer is at least or about 50% more efficient than the HDA primer sequence in a time-to-positivity assay.

In yet a further embodiment the modified HDA primer does not form a hairpin under HDA reaction conditions.

In still another embodiment the modified HDA primer has a melting temperature of about 10 degrees Celsius below the hybridization or amplification temperature of the HDA to about 30 degrees Celsius above the hybridization or amplification temperature of the HDA. In still another embodiment the modified HDA primer has a melting temperature of about 27 to about 67 degrees Celsius. In still another embodiment the modified HDA primer has a melting temperature of about 45 to about 90 degrees Celsius. In still another embodiment the HDA is performed at greater than 50 degrees Celsius. In still another embodiment the HDA is performed at less than 50 degrees Celsius. In still another embodiment the template is an RNA that is reverse transcribed to DNA.

Another aspect of the invention relates to a method of synthesizing the aforementioned modified HDA primer(s).

Another aspect of the invention relates to a modified HDA primer synthesized according to the aforementioned methods.

Yet a further aspect of the invention relates to methods of performing a helicase dependent amplification (HDA) of a template nucleic acid comprising combining in a reaction mixture the nucleic acid template; a forward and a reverse test HDA primer; a helicase; and deoxynucleotide triphosphates (dNTPs); wherein the forward and/or the reverse test HDA primer comprises between three and six M bases at its 5' terminus; and wherein M is adenosine or cytosine; incubating the reaction mixture at an incubation temperature; and obtaining amplified template nucleic acid.

In one embodiment of this aspect of the invention, both the forward and the reverse test HDA primer has between three and six M bases at its 5' terminus. In another embodiment, the HDA is multiplex HDA. In another embodiment the HDA is singleplex HDA. In another embodiment the forward and/or reverse test HDA primer is partially complementary to the template. In another embodiment, the forward and/or reverse test HDA primer is completely complementary to the template. In another embodiment, the forward and/or reverse test HDA primer has between three and six adenosine bases at its 5' terminus. In another embodiment, the forward and/or reverse test HDA primer has between four and six adenosine bases at its 5' terminus. In another embodiment, the forward and/or reverse test HDA primer has either five or six adenosine bases at its 5' terminus. In another embodiment, the forward and/or reverse test HDA primer has either three or four adenosine bases at its 5' terminus. In another embodiment the forward and/or reverse test HDA primer has either four or five adenosine bases at its 5' terminus. In another embodiment, the forward and/or reverse test HDA primer has between three and six cytosine bases at its 5' terminus. In another embodiment, the forward and/or reverse test HDA primer has either five or six cytosine bases at its 5' terminus. In another embodiment, the forward and/or reverse test HDA primer has either three or four cytosine bases at its 5' terminus. In another embodiment, the forward and/or reverse test HDA primer has either four or five cytosine bases at its 5' terminus. In another embodiment, the forward and/or reverse test HDA primer has between four and six cytosine bases at its 5' terminus. In another embodiment, the forward and/or reverse test HDA primer has either five or six M bases at its 5' terminus. In another embodiment, the forward and/or reverse test HDA primer has either three or four M bases at its 5' terminus. In another embodiment, the forward and/or reverse test HDA primer has either four or five M bases at its 5' terminus. In another embodiment, the forward and/or reverse test HDA primer has between four and six M bases at its 5' terminus. In another embodiment, the modified HDA primer the HDA has greater amplification efficiency than if the same reaction were carried out with at least one control forward primer; wherein the only difference between the test forward HDA primer and the control forward primer being that the control primer lacks the between three and six M bases at its 5' terminus. In another embodiment the wherein HDA has greater amplification efficiency than if the same reaction were carried out with at least one control reverse primer; wherein the only difference between the test reverse HDA primer and the control reverse primer being that the control primer lacks the between three and six M bases at its 5' terminus. In another embodiment, the amplification efficiency is at least or about 10%, 20%, 40%, 50%, or greater in a time-to-positivity assay.

Another aspect of the invention relates to a kit for performing a helicase dependent amplification (HDA) of a template nucleic acid comprising HDA reagents comprising a forward and a reverse test HDA primer; wherein the forward and/or the reverse test HDA primer comprises between three and six M bases at its 5' terminus; and wherein M is adenosine or cytosine.

In one embodiment of this aspect of the invention, the HDA reagents comprise a helicase. In another embodiment, the HDA reagents comprise a thermostable helicase. In another embodiment, the HDA reagents comprise deoxynucleotide triphosphates. In another embodiment, the kit comprises instructions for carrying out the HDA. In another embodiment, the HDA reagents comprise $MgSO_4$ or solutions NaCl. In another embodiment, the HDA reagents comprise single stranded DNA binding proteins. In another embodiment, the HDA reagents comprise a double stranded DNA dye. In another embodiment, the HDA reagents are lyophilized.

Another aspect of the invention relates to a method of making a primer for helicase dependent amplification (HDA) of a template nucleic acid comprising identifying a target sequence on the template nucleic acid to be amplified; identifying a primer sequence to amplify the target sequence; and making the primer; wherein the primer comprises between three and six M bases at its 5' terminus; and wherein M is adenosine or cytosine.

In one embodiment of this aspect of the invention the primer is completely complementary to the template. In another embodiment, the primer is about or at least 70% complementary to the target sequence. In another embodiment, the primer is about or at least 70, 90, 95 or 99% complementary to the target sequence.

In another embodiment of this aspect of the invention, the method comprises ligating an enriched 5' terminal portion the primer to give it three and six M bases at its 5' terminus; and wherein M is adenosine or cytosine.

These and other aspects and embodiments which will be apparent to those of skill in the art upon reading the specification.

BRIEF DESCRIPTION OF THE FIGURES

A more complete understanding of the present invention may be obtained by reference to the accompanying drawings, when considered in conjunction with the subsequent detailed description. The embodiments illustrated in the drawings are intended only to exemplify the invention and should not be construed as limiting the invention to the illustrated embodiments, in which:

FIG. 1. Shows the results of a time-to-positivity assay described in Example 1.

FIG. 2. Shows the results of a time-to-positivity assay described in Example 2.

FIG. 3. Shows the results of a time-to-positivity assay described in Example 3.

DETAILED DESCRIPTION OF THE INVENTION

Helicase is a nucleic acid unwinding enzyme that primarily acts from the termini of an amplicon. Consequently, it was heretofore assumed that the melting behaviors of the ends of an amplicon are crucial for efficient helicase activity. In particular, it was assumed that because of their increased hydrogen bonding, GC rich ends reduced helicase-mediated strand separation efficiency.

It has unexpectedly and surprisingly been found that HDA primers having termini enriched for A or C at the 5'-ends, resulted in a much more efficient HDA reaction than those primers having G or T rich 5'-ends. Since A is a low melting base and C is a high-melting base, the melting characteristic of primer termini is not correlated with melting characteristics of amplicon termini.

The term "HDA" refers to Helicase Dependent Amplification which is an in vitro method for amplifying nucleic acids by using a helicase preparation for unwinding a double stranded nucleic acid to generate templates for primer hybridization and subsequent primer-extension. This process utilizes at least two oligonucleotide primers, each hybridizing to the 3'-end of either the sense strand containing the target sequence or the anti-sense strand containing the reverse-complementary target sequence. The HDA reaction is a general method for helicase-dependent nucleic acid amplification.

The term "nucleic acid" refers to double stranded or single stranded DNA, RNA molecules or DNA/RNA hybrids. Those molecules which are double stranded nucleic acid molecules may be nicked or intact. The double stranded or single stranded nucleic acid molecules may be linear or circular. The duplexes may be blunt ended or have single stranded tails. The single stranded molecules may have secondary structure in the form of hairpins or loops and stems. The nucleic acid may be isolated from a variety of sources including the environment, food, agriculture, fermentations, biological fluids such as blood, milk, cerebrospinal fluid, sputum, saliva, stool, lung aspirates, swabs of mucosal tissues or tissue samples or cells. Nucleic acid samples may obtained from cells or viruses and may include any of: chromosomal DNA, extra chromosomal DNA including plasmid DNA, recombinant DNA, DNA fragments, messenger RNA, transfer RNA, ribosomal RNA, double stranded RNA or other RNAs that occur in cells or viruses. The nucleic acid may be isolated, cloned or synthesized in vitro by means of chemical synthesis. Any of the above described nucleic acids may be subject to modification where individual nucleotides within the nucleic acid are chemically altered (for example, by methylation). Modifications may arise naturally or by in vitro synthesis. The term "duplex" refers to a nucleic acid molecule that is double stranded in whole or part.

The term "target" or "template" nucleic acid refers to a whole or part of nucleic acid to be selectively amplified and which is defined by 3' and 5' boundaries. The target nucleic acid may also be referred to as a fragment or sequence that is intended to be amplified. The size of the target nucleic acid to be amplified may be, for example, in the range of about or at least 50 to 1000, 50 to 500, 50 to 250, 75 to 150 bases or kilobases. The target nucleic acid may be contained within a longer double stranded or single stranded nucleic acid. Alternatively, the target nucleic acid may be an entire double stranded or single stranded nucleic acid. The template can also be modified nucleic acid, e.g. by organic groups such as methyl groups, biotin, formaldehyde modified nucleic acids, and such.

If RNA is used as a template, reverse transcription into cDNA have to be performed prior to initiation HDA. Synthesis of cDNA may be performed prior to HDA in a different reaction and/or different reaction milieuu (two-step process) or can be performed within the HDA reagents (one-step process). The target nucleic acid may be damaged and may repaired prior amplification (e.g. repair of abasic sites). The target nucleic acid may have no primer binding site. In this case the missing primer binding site may be attached e.g. by ligation so that HDA can be performed.

The terms "melting," "unwinding" or "denaturing" refer to separating all or part of two complementary strands of a nucleic acid duplex.

The term of "hybridization" refers to binding of an oligonucleotide primer to a region of the single-stranded nucleic acid template under the conditions in which primer binds only specifically to its complementary sequence on one of the template strands, not other regions in the template. The specificity of hybridization may be influenced by inter alia, the length of the oligonucleotide primer, the temperature in which the hybridization reaction is performed, the ionic strength, GC content and the pH.

The term "primer" refers to a single stranded nucleic acid capable of binding to a single stranded region on a target nucleic acid to facilitate polymerase dependent replication of the target nucleic acid. The invention envisages the use of a forward and a reverse primer. Preferably, the primers described herein do not or are not predicted to form secondary structures, complete or partial hairpins, in any given phase of an HDA reaction (e.g., during melting, hybridization/annealing and/or extension).

Generally, primer pairs suitable for use in HDA are short synthetic oligonucleotides, for example, having a length of exactly, about or at least 8, 9, 10, 11, 12, 13, 14, 15, 16, 17, 18, 19, 20, 22, 23, 24, 25, 26, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, or more nucleotide bases. Preferably the primers are between about 5 and 60, 10 and 50, 15 and 30 nucleotide bases.

Oligonucleotide primer design involves various parameters such as string-based alignment scores, melting temperature, primer length and GC content (Kampke et al., Bioinformatics 17:214-225 (2003)). When designing a primer, one of the important factors is to choose a sequence within the target fragment which is specific to the nucleic acid molecule to be amplified. The other important factor is to decide the melting temperature of a primer for HDA reaction. The melting temperature of a primer is determined by the length and GC content of that oligonucleotide. Preferably the melting temperature of a primer is exactly, about or at least 3, 4, 5, 6, 7, 8, 9, 10, 11, 12, 13, 14, 15, 16, 17, 18, 19, 20, 22, 23, 24, 25, 26, 26, 27, 28, 29, 30, 31, 32, 33, 34, 35, 36, 37, 38, 39, 40, 41, 42, 43, 44, 45, 46, 47, 48, 49, or 50 degrees Celsius above or below the temperature at which the hybridization and amplification will take place. More preferably, the melting temperature is about 10 degrees Celsius below the hybridization or amplification temperature of the HDA to 30 degrees Celsius above the hybridization or amplification temperature of the HDA, or 15 degrees Celsius below the hybridization or amplification temperature of the HDA to 25 degrees Celsius above than the temperature at which the hybridization and amplification will take place. For example, if the temperature of the hybridization and amplification is set at 37 degrees Celsius when using the E. coli UvrD helicase preparation, the melting temperature of a pair of primers designed for this reaction should be in a range between about 27 degrees Celsius to about 67 degrees Celsius.

In certain embodiments, when the temperature of the hybridization and amplification is 60 degree Celsius, the melting temperature of a pair of primers designed for that reaction should be in a range between 45 and 90 degrees Celsius. To choose the best primer for a HDA reaction, a set of primers with various melting temperatures can be tested in a parallel assays. More information regarding primer design is described by Kampke et al., Bioinformatics 17:214-225 (2003).

In certain embodiments, each primer hybridizes to each end of the target nucleic acid and may be extended in a 3' to 5' direction by a polymerase using the target nucleotide sequence as a template (FIG. 3). Conditions of hybridization are standard as described in "Molecular Cloning and Laboratory Manual" $2^{nd}$ Sambrook, Rich and Maniatis, pub. Cold Spring Harbor (2003). To achieve specific amplification, a homologous or perfect match primer may be used.

Preferably, however, primers may include sequences at their 5' end which are non-complementary to the target nucleotide sequence(s). Alternatively, primers may contain nucleotides or sequences throughout that are not exactly complementary to the target nucleic acid. Primers may represent analogous primers or may be non-specific or universal primers for use in HDA as long as specific hybridization can be achieved by the primer-template binding at a predetermined temperature.

The optimized HDA primers of the invention preferably have "enriched 5' terminal portions" that are enriched for adenosine, cytosine or a mixture thereof. In one embodiment, the 5' terminal portion consists of at least 2, 3, 4, 5, 6, 7, 8, 9, 10 or more nucleotides at the 5' terminus of a primer. Preferably, the enriched 5' terminal portion consists of at least 3 to 6, 4 to 6, or 3 to 5 nucleotides at the 5' terminus of a primer. "Enriched" in this context means that at least or about 70, 75, 80, 85, 90, 91, 92, 93, 94, 95, 96, 97, 98% of the nucleotides in the enriched 5' terminal portion are adenosine, cytosine or a mixture thereof. The nucleotides of the enriched 5' terminal portions of such primers may or may not be completely complementary to the target nucleic acid being amplified.

In one embodiment, an existing HDA primer is modified and optimized for performance by adding, deleting and/or substituting certain nucleotides in the 5' terminus of the HDA primer so that the 5' terminal portion is modified to be an "enriched 5' terminal portion" as defined above. In another embodiment, adenosine and/or cytosine bases are grafted, e.g., ligated, onto the 5' terminus of an HDA primer thereby providing it with an enriched 5' terminal portion.

In various embodiments, the primers may include any of the deoxyribonucleotide bases A, T, G or C and/or one or more ribonucleotide bases, A, C, U, G and/or one or more modified nucleotide (deoxyribonucleotide or ribonucleotide) wherein the modification does not prevent hybridization of the primer to the nucleic acid or elongation of the primer or denaturation of double stranded molecules. Primers may be modified with chemical groups such as phosphorothioates or methylphosphonates or with non-nucleotide linkers to enhance their performance or to facilitate the characterization of amplification products. Primers may bear abasic sites. Primers can also be modified by addition of covalently bound functional organic groups e.g. addition of fluorophores, biotin, aminoallyl or other such functional modifications.

In various embodiments, to detect amplified products, the primers may be subject to modification, such as fluorescent or chemiluminescent-labeling, and biotinylation (for example, fluorescent tags such as amine reactive fluorescein ester of carboxyfluorescein—Glen Research, Sterling, Va.). Other labeling methods include radioactive isotopes, chromophores and ligands such as biotin or haptens which while not directly detectable can be readily detected by reaction with labeled forms of their specific binding partners e.g., avidin and antibodies respectively.

Primers as described herein can be prepared by methods known in the art. (see, for example U.S. Pat. No. 6,214,587).

In some embodiments, a pair of two sequence-specific primers, one hybridizing to the 5'-border of the target sequence (forward primer) and the other hybridizing to the 3'-border of the target (reverse primer) are used in HDA to achieve exponential amplification of a target sequence. Multiple pairs of primers can be utilized in a single HDA reaction for amplifying multiple targets simultaneously using different detection tags in a multiplex reaction. Multiplexing is commonly used in SNP analysis and in detecting pathogens (Jessing et al., J. Clin. Microbiol. 41:4095-4100 (2003)).

The term "accessory protein" refers to any protein capable of stimulating helicase activity. For example, *E. coli* MutL protein is an accessory protein (Yamaguchi et al. J. Biol. Chem. 273:9197-9201 (1998); Mechanic et al., J. Biol. Chem. 275:38337-38346 (2000)) for enhancing UvrD helicase melting activity. In embodiments of the method, accessory proteins are desirable for use with selected helicases. In alternative embodiments, unwinding of nucleic acids may be achieved by helicases in the absence of accessory proteins.

The term "cofactor" refers to small-molecule agents that are required for the helicase unwinding activity. Helicase cofactors include nucleoside triphosphate (NTP) and deoxynucleoside triphosphate (dNTP) and magnesium (or other divalent cations). For example, ATP (adenosine triphosphate) may be used as a cofactor for UvrD helicase at a concentration in the range of 0.1-100 mM and preferably in the range of 1 to 10 mM (for example 3 mM). Similarly, dTTP (deoxythymidine triphosphate) may be used as a cofactor for T7 Gp4B helicase in the range of 1-10 mM (for example 3 mM).

The term "helicase" refers here to any enzyme capable of unwinding a double stranded nucleic acid enzymatically. For example, helicases are enzymes that are found in all organisms and in all processes that involve nucleic acid such as replication, recombination, repair, transcription, translation and RNA splicing. (Kornberg and Baker, DNA Replication, W.H. Freeman and Company ($2^{nd}$ ed. (1992)), especially chapter 11). Any helicase that translocates along DNA or RNA in a 5' to 3' direction or in the opposite 3' to 5' direction may be used in present embodiments of the invention. This includes helicases obtained from prokaryotes, viruses, archaea, and eukaryotes or recombinant forms of naturally occurring enzymes as well as analogues or derivatives having the specified activity. Examples of naturally occurring DNA helicases, described by Kornberg and Baker in chapter 11 of their book, DNA Replication, W.H. Freeman and Company ($2^{nd}$ ed. (1992)), include *E. coli* helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful in HDA include RecQ helicase (Harmon and Kowalczykowski, J. Biol. Chem. 276:232-243 (2001)), thermostable UvrD helicases from *T. tengcongensis* and *T. thermophilus* (Collins and McCarthy, Extremophiles. 7:35-41. (2003)), thermostable DnaB helicase from *T. aquaticus* (Kaplan and Steitz, J. Biol. Chem. 274:6889-6897 (1999)), and MCM helicase from archaeal and eukaryotic organisms ((Grainge et al., Nucleic Acids Res. 31:4888-4898 (2003)).

Non-limiting examples of helicases for use in present embodiments may also be found at the following web address: blocks.fhcrc.org (Get Blocks by Keyword: helicase). This site lists 49 Herpes helicases, 224 DnaB helicases, 250 UvrD-helicases and UvrD/Rep helicases, 276 DEAH_ATP-dependent helicases ("DEAH" disclosed as SEQ ID NO: 45), 147 Papillom_E1 Papillomavirus helicase E1 protein, 608 Viral helicase1 Viral (superfamily 1) RNA helicases and 556 DEAD_ATP-dependent helicases ("DEAD" disclosed as SEQ ID NO: 46). Examples of helicases that generally replicate in a 5' to 3' direction are T7 Gp4 helicase, DnaB helicase and Rho helicase, while examples of helicases that replicate in the 3'-5' direction include UvrD helicase, PcrA, Rep, NS3 RNA helicase of HCV.

Originally, HDA was described by using UvrD like helicases from different organisms like *E. coli* or *Thermoanaerobacter tengcongensis*. Other helicase may be of equal functionality in HDA e.g PcrA (*Staphylococcus*), RecD or Rep from *E. coli*, Dda (T4-phage), or others In a preferred embodiment of the invention, the helicase is provided in a "helicase preparation." The helicase preparation refers to a mixture of reagents which when combined with a DNA polymerase, a nucleic acid template, four deoxynucleotide triphosphates, and primers are capable of achieving isothermal, exponential and specific nucleic acid amplification in vitro.

More particularly, the helicase preparation includes a helicase, an energy source such as a nucleotide triphosphate (NTP) or deoxynucleotide triphosphate (dNTP), and a single strand DNA binding protein (SSB). One or more additional reagents may be included in the helicase preparation, where these are selected from the following: one or more additional helicases, an accessory protein, small molecules, chemical reagents and a buffer.

Where a thermostable helicase is utilized in a helicase preparation, the presence of a single stranded binding protein is optional.

The term "HDA system" or "HDA kit" is used herein to describe a group of interacting elements for performing the function of amplifying nucleic acids according to the Helicase-Dependent Amplification method described herein. The HDA system includes HDA reagents such as a forward and reverse primer, a helicase preparation, a polymerase and optionally a topoisomerase.

HDA reagents can also include DNA binding proteins (e.g. SSB, MutS, MutL or others), BSA, pyrophosphatase, kinases, other polymerases, a reverse transcriptase (to convert RNA template to DNA prior to HDA amplification), sugars, sugar alcohols, polymers (e.g. PEG, dextrose, polymers from natural source e.g. from algae, plants fungi, enzymes to repair target nucleic acid prior amplification, cofactors and/or accessory proteins.

The HDA reagents may also include uracil-N-glycosylase (UNG), a DNA repair enzyme that hydrolyzes the base-ribose bond at uracil residues, can be used to eliminate DNA contamination from previously amplified PCR products. UNG treatment prevents replication of uracil-containing DNA by causing the DNA polymerase to stall at the resulting abasic sites. For UNG to be effective against contamination, the products of previous amplifications may be synthesized in the presence of dUTP. This is may be accomplished by substituting dUTP for some or all of the dTTP in the reaction.

For example, the UvrD HDA system may be constituted by mixing together, a UvrD helicase preparation (for example, an *E. coli* UvrD helicase preparation or a Tte-UvrD helicase preparation) and a DNA polymerase such as Exo⁻ Klenow Fragment, DNA polymerase Large fragment, Exo⁺ Klenow Fragment or T7 Sequenase.

Another example is the T7 HDA system which includes a T7 helicase preparation (T7 Gp4B helicase, T7 Gp2.5 SSB, and dTTP), and T7 Sequenase.

Another example is RecBCD HDA system which includes a RecBCD preparation (RecBCD helicase with T4gp 32) and T7 Sequenase.

Any selected HDA system may be optimized by substitution, addition, or subtraction of elements within the mixture as discussed in more detail below.

Helicases show improved activity in the presence of single-strand binding proteins (SSB). In these circumstances, the choice of SSB is generally not limited to a specific protein. Examples of single strand binding proteins are T4 gene 32 protein, *E. coli* SSB, T7 gp2.5 SSB, phage phi29 SSB (Kornberg and Baker, supra (1992)) and truncated forms of the aforementioned.

In addition to salt and pH, other chemical reagents, such as denaturation reagents including urea and dimethyl-sulfoxide (DMSO) can be added to the HDA reaction to partially denature or destabilize the duplex DNA. HDA reactions can be compared in different concentrations of denaturation reagents with or without SSB protein. In this way, chemical compounds can be identified which increase HDA efficiency and/or substitute for SSB in single-strand (ss) DNA stabilization. Most of the biomacromolecules such as nucleic acids and proteins are designed to function and/or form their native structures in a living cell at much higher concentrations than in vitro experimental conditions. Polyethylene glycol (PEG) has been used to create an artificial molecular crowding condition by excluding water and creating electrostatic interaction with solute polycations (Miyoshi, et al., Biochemistry 41:15017-15024 (2002)). When PEG (7.5%) is added to a DNA ligation reaction, the reaction time is reduced to 5 min (Quick Ligation Kit, New England Biolabs, Inc. (Beverly, Mass.)). PEG has also been added into helicase unwinding assays to increase the efficiency of the reaction (Dong, et al., Proc. Natl. Acad. Sci. USA 93:14456-14461 (1996)). PEG or other molecular crowding reagents on HDA may increase the effective concentrations of enzymes and nucleic acids in HDA reaction and thus reduce the reaction time and amount of protein concentration needed for the reaction.

As such, HDA reagents may also include facilitators of amplification such as betain (about 0.1-2M), MgCl or MgSO$_4$, (about 1.0-10.0 mM Mg2+), DMSO (about 1-20%), formamide (about 0.1-10%), BSA (about 0.1-1 mg/ml), gelatin (about 0.1-1.0%), (NH$_4$)$_2$SO$_4$ (about 5-40 mM), glycerol (about 5-20%), polyethylene glycol (about 5-15%) and tetramethyl ammonium chloride (about 20-100 mM), and non-ionic detergents (about 0-0.5%) herein the aforementioned concentrations are appropriate for reaction conditions.

ATP or TTP is a commonly preferred energy source for highly processive helicases. On average one ATP molecule is consumed by a DNA helicases to unwind 1 to 4 base pairs (Kornberg and Baker, supra (1992)). In an embodiment of the invention, the UvrD-based HDA system had an optimal initial ATP concentration of 3 mM. To amplify a longer target, more ATP may be consumed as compared to a shorter target. In these circumstances, it may be desirable to include a pyruvate kinase-based ATP regenerating system for use with the helicase (Harmon and Kowalczykowski, Journal of Biological Chemistry 276:232-243 (2001)).

Topoisomerase can be used in long HDA reactions to increase the ability of HDA to amplify long target amplicons. When a very long linear DNA duplex is separated by a helicase, the swivel (relaxing) function of a topoisomerase removes the twist and prevents over-winding (Kornberg and Baker, supra (1992)). For example, *E. coli* topoisomerase I (Fermentas, Vilnius, Lithuania) can be used to relax negatively supercoiled DNA by introducing a nick into one DNA strand. In contrast, *E. Coli* DNA gyrase (topoisomerase II) introduces a transient double-stranded break into DNA allowing DNA strands to pass through one another (Kornberg and Baker, supra (1992)).

Amplified nucleic acid product may be detected by various methods including ethidium-bromide staining and detecting the amplified sequence by means of a label selected from the group consisting of a radiolabel, a fluorescent-label, and an enzyme. For example HDA amplified products can be detected in real-time using fluorescent-labeled LUX™ Primers (Invitrogen Corporation, Carlsbad, Calif.) which are oligonucleotides designed with a fluorophore close to the 3' end in a hairpin structure. This configuration intrinsically renders fluorescence quenching capability without separate quenching moiety. When the primer becomes incorporated into double-stranded amplification product, the fluorophore is dequenched, resulting in a significant increase in fluorescent signal.

Although other isothermal nucleic acid amplification methods such as Strand-Displacement Amplification can amplify target at a constant temperature without thermocycling, they do require an initial denaturation step to generate single-stranded template. An advantage of embodiments of the method described herein is that both unwinding by helicase and amplification can effectively occur at a single temperature throughout. Alternatively, the temperature is raised to assist initial unwinding of the target nucleic acid by the helicase and the amplification then proceeds at a single temperature.

HDA can be used in place of PCR for amplification of reverse transcribed product of RNA. In addition, HDA is useful for quantitative amplification such as found to be useful in gene expression studies and environmental analyses. Accordingly, where it is desirable to determine the amounts of a target nucleic acid, HDA can be utilized in a real time end point assay. Accordingly, HDA may be used to determine the relative amounts of messenger RNA in a cell in gene expression studies. For example, calibrated gene expression profiles described in WO 0125473 can be generated using quantitative helicase dependent amplification or Q-HDA.

Real time HDA may be used as a sensitive technique to determine amounts of an organism in a contaminated sample such as *E. coli* in seawater. Real time detection using sensitive markers such as fluorescence in a HDA reaction.

HDA may be used in the context of a compact device for use in field activities and/or laboratory diagnoses. For example, HDA may be practiced in a microfluidic environment. Microfluidics technologies (lab on a chip) are rapidly emerging as key strategies for cost and time saving by performing biochemical analyses in miniaturized environment usually at nanoliter scale. Microfluidics technologies have great potential to be used as field-portable equipment in pathogen detection when combining with a nucleic acid amplification and detection method. The ability of HDA to amplify nucleic acids in an isothermal condition without initial heat-denaturation makes it a good candidate for the nucleic acid amplification process in a microfluidic device. Similarly, HDA may be used either in kits or in laboratory amplification procedures to create response profiles of the sort described in International Publication No. WO 0202740 or for monitoring disease (U.S. Publication No. 2001018182).

HDA may be used for amplifying target nucleic acid from different sources and having different sequences. For example, longer target sequence (>2 kb) can be amplified by the T7 Gp4B-based HDA system. The method of using Helicase-Dependent Amplification to amplify nucleic acids can be performed using different helicase preparations, such as a helicase preparation containing T7 Gp4B helicase, or a helicase preparation containing more than one helicase, such as T7 Gp4B helicase and UvrD helicase.

The ability of HDA to amplify of as little as 10 copies of bacterial genomic DNA supports the use of HDA for molecular diagnostics application of infectious diseases caused by pathogenic bacteria, for example *Chlamydia trachomatis* and *Neisseria gonorrhoeae*. The demonstration that target sequences can be amplified from human genomic DNA samples supports the use of HDA in identifying genetic alleles corresponding to a particular disease including single nucleotide polymorphisms and forensic applications that rely on characterizing small amounts of nucleic acid at the scene of a crime or at an archeological site.

"Isothermal amplification" refers to amplification which occurs at a single temperature. This does not include the single brief time period (less than 15 minutes) at the initiation of amplification which may be conducted at the same temperature as the amplification procedure or at a higher temperature. Depending on the source of enzymes that are used for HDA, the reaction can be performed a low temperatures (<50° C.) e.g., at least or about 30, 31, 32, 33, 34, 35, 36, 37, 38, 39, 40, 41, 42, 43, 44, 45, 46, 47, 48, 49 degrees Celsius; or at high temperatures (≥50° C.), e.g., at least or about 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115 or more degrees Celsius.

The term "more efficient control in a time-to-positivity" reaction refers to the fact that HDA primers modified to have an enriched 5' terminal portion are better at facilitating a HDA reaction than HDA primers lacking such an enriched 5' terminal portions. Time-to-positivity reactions are those HDA reactions in which the time from the beginning of the reaction until the reaction amplification products are detectable, is measured. The less time elapses the more efficient the reaction has proceeded. As such, the time to positivity is a measure of efficiency. In one embodiment, if a modified HDA primer having an enriched 5' terminal portion facilitates a time-to-positivity reaction taking 10 minutes compared to 15 minutes for the same control HDA primer lacking such an enriched 5' terminal portion, the modified HDA primer is 33% more efficient than the control primer.

In a preferred embodiment, the HDA primers modified to have an enriched 5' terminal portion are about or at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 120, 130, 14, 150, 175, 200, 225, 250, 275, 300, 350, 375, 400, 425, 450, 475, 500, 550, 600, 700, 800, 900 or 1000 percent more efficient than the same primer lacking an enriched 5' terminal portion in the same HDA "time-to-positivity" reaction.

In one embodiment, the reaction products are detectable using a fluorescent DNA dye such as ethidium bromide or SYBR Green for example. In another embodiment, the time-to-positivity reaction is carried out in a real time PCR machine.

EXAMPLE 1

Characterization of Amplicon Ends with Best HDA Efficiency

HDA efficiency is measured by the reaction time (Real-time HDA) that is needed to detect a positive signal. The ends of amplicons are modified by extra bases. The primers used are indicated in the Tables below.

Set Up:
DNA synthesized from human RNA was used in a tHDA reaction using the forward (F) and reverse (R) primer sets as indicted below. The reaction was performed in a buffer (pH 8.8) comprising 0.4 mM dNTPs (each A, G, C, and T), and additional 3 mM dATP, 10 mM KCl, 40 mM NaCl, 3.5 mM $MgCl_2$. 0.16 μM forward primer (F) and 0.48 μM reverse primer (R) were used as primers. Helicase and Polymerase was provided by BioHelix. The 25 μl HDA reaction using 5 μl cDNA was performed at a constant temperature of 63° C. for 90 min. A Real-time PCR instrument was used to monitor the fluorescence that was generated with increasing amount of amplified amplicon sequence during HDA reaction. Time to positive result was measured (time-to-positivity) in minutes. Each reaction was set up in triplicate.

| | |
|---|---|
| ARAF_F | TCGTTTGGCACCGTGTTTC (SEQ ID NO: 1) |
| ARAF_R | GGGACACCTTGAGCACCTTC (SEQ ID NO: 2) |
| ARAF_F_A1 | ATC GTT TGG CAC CGT GTT TC (SEQ ID NO: 3) |
| ARAF_R_A1 | AGG GAC ACC TTG AGC ACC TTC (SEQ ID NO: 4) |
| ARAF_F_A2 | AAT CGT TTG GCA CCG TGT TTC (SEQ ID NO: 5) |
| ARAF_R_A2 | AAG GGA CAC CTT GAG CAC CTT C (SEQ ID NO: 6) |
| ARAF_F_A3 | AAA TCG TTT GGC ACC GTG TTT C (SEQ ID NO: 7) |
| ARAF_R_A3 | AAA GGG ACA CCT TGA GCA CCT TC (SEQ ID NO: 8) |
| ARAF_F_C1 | CTC GTT TGG CAC CGT GTT TC (SEQ ID NO: 9) |
| ARAF_R_C1 | CGG GAC ACC TTG AGC ACC TTC (SEQ ID NO: 10) |
| ARAF_F_C2 | CCT CGT TTG GCA CCG TGT TTC (SEQ ID NO: 11) |
| ARAF_R_C2 | CCG GGA CAC CTT GAG CAC CTT C (SEQ ID NO: 12) |
| ARAF_F_C3 | CCC TCG TTT GGC ACC GTG TTT C (SEQ ID NO: 13) |
| ARAF_R_C3 | CCC GGG ACA CCT TGA GCA CCT TC (SEQ ID NO: 14) |
| ARAF_F_G1 | GTC GTT TGG CAC CGT GTT TC (SEQ ID NO: 15) |
| ARAF_R_G1 | GGG GAC ACC TTG AGC ACC TTC (SEQ ID NO: 16) |
| ARAF_F_G2 | GGT CGT TTG GCA CCG TGT TTV (SEQ ID NO: 17) |
| ARAF_R_G2 | GGG GGA CAC CTT GAG CAC CTT C (SEQ ID NO: 18) |
| ARAF_F_T3 | TTT TCG TTT GGC ACC GTG TTT C (SEQ ID NO: 19) |
| ARAF_R_T3 | TTT GGG ACA CCT TGA GCA CCT TC (SEQ ID NO: 20) |
| ARAF ROX IOWA Probe | CGGTGGCATGGCGATGTGGCCGT (SEQ ID NO: 21) |

Result:
The fastest HDA reactions can be obtained using primers having 3 A-bases or 3 C-bases at their 5'-termini. Lowering the numbers of A-bases results in a decrease of reaction kinetics from 12.9 minutes (A3) to 15.3 min (A1) or 22.7 min (Std., no 5'-A), Decreasing the numbers of C-bases in the primers results in a decrease of reaction time from 16.6 minutes (C3) to 20.0 min (C1) or 22.7 min (Std. no 5'-C). Primers having additional 3 T-bases or 2 G-bases at their 5'-end resulted in a further slowdown to 24.3 or 69.2 min.

Conclusion Experiment 1:
HDA primers having A- or C-Bases at their ends resulted in increased HDA efficiency measured by time to positive result (time-to-positivity, min).

EXAMPLE 2

Characterization of Amplicon Ends with Best HDA Efficiency

Set Up:
cDNA synthesized from human RNA was used in tHDA reaction using different primer sets as indicted below. The reaction was performed in a buffer (pH 8.8) comprising 0.4 mM dNTPs (each A, G, C, and T), and additional 3 mM dATP, 10 mM KCl, 40 mM NaCl, 3.5 mM $MgCl_2$. 0.16 μM forward primer (F) and 0.48 μM reverse primer (R) were used as primers. Helicase and Polymerase was provided by BioHelix. The 25 μl HDA reaction using 5 μl cDNA was performed at a constant temperature of 63° C. for 90 min. A Real-time PCR instrument was used to monitor the fluorescence that was generated with increasing amount of amplified amplicon sequence during HDA reaction. Time to positive result was measured (time-to-positivity) in minutes. Each reaction was set up in triplicate.

| | |
|---|---|
| ARAF_F | TCGTTTGGCACCGTTTC (SEQ ID NO: 22) |
| ARAF_R | GGGACACCTTGAGCACCTTC (SEQ ID NO: 23) |
| ARAF_F_A3 | AAATCGTTTGGCACCGTGTTTC (SEQ ID NO: 24) |
| ARAF_R_A3 | AAAGGGACACCTTGAGCACCTTC (SEQ ID NO: 25) |
| ARAF ROX IOWA Probe | CGGTGGCATGGCGATGTGGCCGT (SEQ ID NO: 21) |

Results:

The fastest HDA reactions can be obtained utilizing primers having 3 A-bases independently whether the forward primer or the reverse primer comprises a 3 A base 5'-terminus. Using a primer pair without the 3 A termini, a time-to-positivity of 34.2 minutes was obtained. Using a primer pair with a 3 A 5'-terminus for the forward primer, a time-to-positivity of 29.0 minutes was obtained. Using a primer pair with a 3 A 5'terminus for the reverse primer, a time-to-positivity of 22.4 minutes was obtained Conclusion:

HDA primers having A-Bases at their 5'-ends resulted in increased HDA efficiency even if only one HDA primer comprises the modified 5'-Terminus.

EXAMPLE 3

Primers having more than 4 A-Bases or C-Bases often did not result in a further improvement of an HDA reaction. Primers with 3 A-Bases or 6 M-Bases (M=A or C) were tested for HDA efficiency. HDA efficiency was measured by reaction time (Real-time HDA) that is needed to detect a positive signal. The ends of the amplicons were modified by extra bases. The different primers used are indicated in the list below.

Set Up:

cDNA synthesized from human RNA was used in tHDA reaction using different primer sets as indicted below. The reaction was performed in a buffer (pH 8.8) comprising 0.4 mM dNTPs (each A, G, C, and T), and additional 3 mM dATP, 10 mM KCl, 40 mM NaCl, 3.5 mM MgCl$_2$. 0.16 µM forward primer (F) and 0.48 µM reverse primer (R) were used as primers. Helicase and Polymerase was provided by BioHelix. The 25 µl HDA reaction using 5 µl cDNA was performed at a constant temperature of 63° C. for 90 min. A Real-time PCR instrument was used to monitor the fluorescence that was generated with increasing amount of amplified amplicon sequence during HDA reaction. Time to positive result was measured (time-to-positivity) in minutes. Each reaction was set up in triplicate.

| | |
|---|---|
| PRDX1_F | TGGGACCCATGAACATTCCTT (SEQ ID NO: 26) |
| PRDX1_R | CCCTGAACGAGATGCCTTCAT (SEQ ID NO: 27) |
| PRDX1_F_A3 | AAATGGGACCCATGAACATTCCTT (SEQ ID NO: 28) |
| PRDX1_R_A3 | AAACCCTGAACGAGATGCCTTCAT (SEQ ID NO: 29) |
| PRDX1 FAM Probe | AGACCCGAAGCGCACCATTGCTCAGGAT (SEQ ID NO: 41) |

Result:

The fastest HDA reactions can be obtained using a primer having 3 A-bases at 5'-Terminus. Primers having 6 A- or C-Bases did not seem to further improve the HDA reaction efficiency. Using a primer pair with forward primer having no A or C bases at the 5'-terminus while reverse primers has 3 C bases at 5'terminus, resulted in a time-to-positivity of 26.9 minutes. Changing the forward primer by a primer that has 3 A bases at 5'terminus, a time-to-positivity of 23.6 minutes was obtained. Changing the reverse primer that has already 3 C bases at 5-terminus by a primer that has 3 A bases in addition to the 3 C bases, the time to positivity was reduced by only 0.7 cycles (compare time to positivity of 26.9 with 26.2). Using the combination of forward primer and reverse primer for HDA, a mixed time-to-positivity of 24.9 minutes was obtained.

Conclusion:

HDA primers having 6 A- or C-Bases did not appear to further improve the HDA reaction compared to primers having 3 A-Bases.

EXAMPLE 4

Determination of the optimal length of 5'-A or C-Tail for HDA primers. Primers having different length of the A-tail (1-6 A-Bases at 5'_terminus) were tested in HDA efficiency. HDA efficiency is measured by reaction time (Real-time HDA) that is needed to detect a positive signal. The ends of the amplicons are modified by extra bases. The different primers used are indicated in the list below.

Set Up:

cDNA synthesized from human RNA was used in tHDA reaction using different primer sets as indicted below. The reaction was performed in a buffer (pH 8.8) comprising 0.4 mM dNTPs (each A, G, C, and T), and additional 3 mM dATP, 10 mM KCl, 40 mM NaCl, 3.5 mM MgCl$_2$. 0.16 µM forward primer (F) and 0.48 µM reverse primer (R) were used as primers. Helicase and Polymerase was provided by BioHelix. The 25 µl HDA reaction using 5 µl cDNA was performed at a constant temperature of 63° C. for 90 min. A Real-time PCR instrument was used to monitor the fluorescence that was generated with increasing amount of amplified amplicon sequence during HDA reaction. Time to positive result was measured (time-to-positivity) in minutes. Each reaction was set up in triplicate.

| | |
|---|---|
| Standard Primer ARAF_F | TCGTTTGGCACCGTGTTTC (SEQ ID NO: 30) |
| Standard Primer ARAF_R | GGGACACCTTGAGCACCTTC (SEQ ID NO: 31) |
| ARAF_F_A1 | ATC GTT TGG CAC CGT GTT TC (SEQ ID NO: 32) |
| ARAF_R_A1 | AGG GAC ACC TTG AGC ACC TTC (SEQ ID NO: 33) |
| ARAF_F_A2 | AAT CGT TTC GCA CCG TGT TTC (SEQ ID NO: 34) |
| ARAF_R_A2 | AAG GGA CAC CTT GAG CAC CTT C (SEQ ID NO: 35) |
| ARAF_F_A3 | AAA TCG TTT GGC ACC GTG TTT C (SEQ ID NO: 36) |
| ARAF_R_A3 | AAA GGG ACA CCT TGA GCA CCT TC (SEQ ID NO: 37) |
| ARAF_F_A4 | AAA ATC GTT TGG CAC CGT GTT TC (SEQ ID NO: 38) |
| ARAF_R_A4 | AAA AGG GAC ACC TTG AGC ACC TTC (SEQ ID NO: 39) |
| ARAF_F_A5 | AAA AAT CGT TTG GCA CCG TGT TTC (SEQ ID NO: 40) |
| ARAF_R_A5 | AAA AAG GGA CAC CTT GAG CAC CTT C (SEQ ID NO: 42) |
| ARAF_F_A6 | AAA AAA TCG TTT GGC ACC GTG TTT C (SEQ ID NO: 43) |
| ARAF_R_A6 | AAA AAA GGG ACA CCT TGA GCA CCT TC (SEQ ID NO: 44) |
| ARAF ROX IOWA Probe | CGGTGGCATGGCGATGTGGCCGT (SEQ ID NO: 21) |

Result:

Fastest HDA reactions can be obtained by primer having 4 A-bases at 5'-Terminus. Primers having 6 A- or C-Bases did seem to not further improve the HDA reaction efficiency. Using a primer pair without the A or C-Bases at the 5'-terminus, a time-to-positivity of 36.6 minutes was obtained. The best time-to-positivity was obtained with 4 A-Bases at 5'-terminus of HDA primers: After 23.9 minutes a positive signal was obtained—that is 12.7 minutes earlier than with standard primers. Further increasing the number of A-Bases within the 5'-terminal A-tail, the HDA efficiency is better than without an A-tail but HDA reaction slowed down slightly compared to reactions having a 4 A-Base tail.

Conclusion:

An HDA primer having a tail of 4 A- or C-Bases are optimal. Longer 5'-tails did not seem to further improve the HDA reaction but can be better compared to primers having no 5'-tail of A- or C-bases.

All references cited above and below are incorporated herein by reference to the extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. A method of performing a helicase dependent amplification (HDA) of a template nucleic acid comprising:
    a. combining in a buffer the template nucleic acid; at least a forward and a reverse test HDA primer; a helicase; and deoxynucleotide triphosphates (dNTPs);
        i. wherein the forward and/or the reverse test HDA primer comprises between three and six M bases at nucleotides 1-6 beginning from the 5' terminus of the primer; and wherein M is adenosine or cytosine;
    b. incubating the reaction mixture at a temperature that is between about 50 degrees Celsius below the melting temperature of the HDA primer to about 3 degrees Celsius above the melting temperature of the HDA primer; and
    c. obtaining amplified template nucleic acid.

2. The method of claim 1 wherein both the forward and the reverse test HDA primer have between three and six M bases at nucleotides 1-6 beginning from the 5' terminus of the primer.

3. The method of claim 1 wherein multiple pairs of primers are utilized in a multiplex HDA reaction.

4. The method of claim 1 wherein the forward and/or reverse test HDA primer is partially or completely complementary to the sequence of the template nucleic acid.

5. The method of claim 1 wherein the forward and/or reverse test HDA primer has between three and six, or between four and six bases at nucleotides 1-6 beginning from the 5' terminus of the primer, said bases consisting of adenosine bases or cytosine bases, or wherein the forward and/or reverse test HDA primer has between three and six M bases at nucleotides 1-6 beginning from the 5' terminus of the primer.

6. The method of claim 1 wherein the HDA has increased amplification efficiency as compared to the same reaction carried out with at least one control forward or reverse primer; wherein the only difference between the test forward HDA primer and the control forward primer being that the control primer lacks the between three and six M bases at its nucleotides 1-6 beginning from the 5' terminus of the primer.

7. The method of claim 6 wherein the amplification efficiency is at least or about 10% greater in a time-to-positivity assay.

8. The method of claim 1 wherein the incubation temperature is between about 30 degrees Celsius below the melting temperature of the HDA primer to about 10 degrees Celsius above the melting temperature of the HDA primer.

* * * * *